United States Patent
Sagi et al.

(10) Patent No.: US 10,066,024 B2
(45) Date of Patent: Sep. 4, 2018

(54) METHODS OF GENERATING ANTIBODIES TO METALLOENZYMES

(75) Inventors: Irit Sagi, Rehovot (IL); Netta Sela-Paswell, Rehovot (IL); Moran Grossman, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 13/882,192

(22) PCT Filed: Oct. 27, 2011

(86) PCT No.: PCT/IL2011/000835
§ 371 (c)(1),
(2), (4) Date: Apr. 28, 2013

(87) PCT Pub. No.: WO2012/056455
PCT Pub. Date: May 3, 2012

(65) Prior Publication Data
US 2013/0209491 A1    Aug. 15, 2013

Related U.S. Application Data

(60) Provisional application No. 61/407,501, filed on Oct. 28, 2010.

(51) Int. Cl.
*C07K 16/40* (2006.01)
*C07K 16/44* (2006.01)

(52) U.S. Cl.
CPC .............. *C07K 16/40* (2013.01); *C07K 16/44* (2013.01); *C07K 2317/76* (2013.01)

(58) Field of Classification Search
None
See application file for complete search history.

(56) References Cited

U.S. PATENT DOCUMENTS

2010/0119520 A1    5/2010  Chen et al.
2010/0227335 A1    9/2010  Baker et al.

FOREIGN PATENT DOCUMENTS

| CN | 101702906 | 5/2010 |
|---|---|---|
| WO | WO 2004/087042 | 10/2004 |
| WO | WO 2008/102359 | 8/2008 |
| WO | WO 2008/103845 | 8/2008 |
| WO | WO 2010/102167 | 9/2010 |
| WO | WO 2011/092700 | 8/2011 |
| WO | WO 2012/056455 | 5/2012 |

OTHER PUBLICATIONS

Vajdos et al. (J Mol Biol. Jul. 5, 2002;320(2):415-28 at 416).*
Brown et al. (J Immunol. May 1996;156(9):3285-91).*
Cruse et al., Illustrated Dict. of Immunology, 2nd ed., CRC Press, 2003; pp. 46, 166, and 382. (Year: 2003).*
NCBI record for Matrilysin preprotein, Accession NP_002414.1, downloaded Oct. 18, 2017 from https://www.ncbi.nlm.nih.gov/protein/NP_002414.1 (Year: 2017).*
International Preliminary Report on Patentability dated May 10, 2013 From the International Bureau of WIPO Re. Application No. PCT/IL2011/000835.
International Search Report and the Written Opinion dated Mar. 2, 2012 From the International Searching Authority Re. Application No. PCT/IL2011/000835.
Sela-Passwell et al. "Antibodies Targeting the Catalytic Zinc Complex of Activated Matrix Metalloproteinases Show Therapeutical Potential", Nature Medicine, XP055019945, 18(1): 143-147, Jan. 1, 2012.
Tallant et al. "Matrix Metalloproteinases: Fold and Function of Their Catalytic Domains", Biochimica et Biophysica Acta, BBA, XP002670043, 1803(1): 20-28, Jan. 2010.
Notification of Office Action dated Jul. 8, 2014 From The State Intellectual Property Office of the People's Republic of China Re. Application No. 2011800630636 and Its Translation Into English.
Search Report dated Jul. 8, 2014 From The State Intellectual Property Office of the People's Republic of China Re. Application No. 2011800630636 and Its Translation Into English.
Notification of Office Action dated May 11, 2015 From The State Intellectual Property Office of the People's Republic of China Re. Application No. 2011800630636 and Its Translation Into English.
Communication Pursuant to Article 94(3) EPC dated Aug. 14, 2014 From the European Patent Office Re. Application No. 11793503.1.
Office Action dated Jan. 7, 2016 From the Israel Patent Office Re. Application No. 226040 and Its Translation Into English.
Communication Pursuant to Article 94(3) EPC dated May 4, 2016 From the European Patent Office Re. Application No. 11793503.1.
Shiomi et al. "MT1-MMP and MMP-7 in Invasion and Metastasis of Human Cancers", Cancer and Metastasis Reviews, 22(2-3): 145-152, Jun. 2003.
Smyth "The Trouble With Inhibitors", Signalling Scissors: New Perspectives on Proteases, XP055269542, p. 1-4, Oct. 2003.
Communication Pursuant to Article 94(3) EPC dated Mar. 9, 2017 From the European Patent Office Re. Application No. 11793503.1. (6 Pages).

* cited by examiner

*Primary Examiner* — Brian J Gangle
*Assistant Examiner* — Andrea K McCollum

(57) ABSTRACT

A method of generating an antibody which inhibits a metalloenzyme is disclosed. The method comprises immunizing a subject with:
(i) a synthetic zinc mimicry compound having structural and electronic properties similar to a catalytic domain of the metalloenzyme; and
(ii) the metalloenzyme,
Antibodies generated by this method are also disclosed as well as uses thereof.

4 Claims, 1 Drawing Sheet
(1 of 1 Drawing Sheet(s) Filed in Color)

METHODS OF GENERATING ANTIBODIES TO METALLOENZYMES

RELATED APPLICATIONS

This application is a National Phase of PCT Patent Application No. PCT/IL2011/000835 having International filing date of Oct. 27, 2011, which claims the benefit of priority under 35 USC § 119(e) of U.S. Provisional Patent Application No. 61/407,501 filed on Oct. 28, 2010. The contents of the above applications are all incorporated by reference as if fully set forth herein in their entirety.

FIELD AND BACKGROUND OF THE INVENTION

The present invention, in some embodiments thereof, relates to methods of generating antibodies to metalloenzymes, more particularly, but not exclusively, to MMP-7 and anthrax lethal factor (ALF).

The matrix metalloproteins (MMPs) are key enzymes participating in remodeling of the extracellular matrix (ECM). These enzymes are capable of destroying a variety of connective tissue components of articular cartilage or basement membranes.

The human MMP gene family consists of at least 28 structurally related proteins, which share a similar overall spherical topology. Each MMP is secreted as an inactive, latent pro-enzyme. The catalytic zinc domain is composed of about 180 amino acids wherein the highly conserved sequence HE-GH-LGL-H provides the three histidine (i.e., H) residues which bind to the metal Zn(2+) ion. The forth-binding site of the catalytic zinc ion in the pro-enzyme is bound to a cystein residue (Morgunova et al., 1999), which upon enzyme activation dissociates from the active site (Van Wart and Birkedal-Hansen, 1990). As a result, the forth-binding site in the activated MMPs is taken up by a water molecule, which is also hydrogen-bonded to a conserved glutamic residue. This process facilitates the hydrolysis of a peptide bond of the target substrate with the activated water molecule.

MMP-7 (also referred to in the literature as "matrilysin") is expressed in epithelial cells of normal and diseased tissues, and is capable of digesting a large series of proteins located in the extracellular matrix. These include collagen IV and X, gelatin, casein, laminin, aggrecan, entactin, elastin and versican. MMP-7 appears to play a role in the activation of other proteinases such as plasminogen, MMP-1, MMP-2, and MMP9. In addition to its role in connective tissue remodeling, MMP-7 has been shown to be expressed in some malignant tumors and may play an important role in tumor invasion and metastasis. Structurally, MMP-7 is the smallest of the MMPs and consists of two domains: a pro-domain that is cleaved upon activation and a catalytic domain containing the zinc-binding site. Several publications have shown that the MMP proteins, and in particular MMP-7, are implicated in ovarian and other cancers such as renal cell carcinoma. It has also been suggested to be a candidate biomarker for ovarian cancer—see, for example, Wang et al. (2005) Int. J. Cancer 114(1):19-31; Wang et al. (2006) Int. J. Cancer 118(4):879-88; Maurel et al. (2007) Int. J. Cancer 121(5): 1066-1071; and Sarkissian et al. (2008) Clin. Chem. 54(3): 574-581.

Anthrax is a highly lethal infectious disease caused by the spore-forming bacterium *Bacillus anthracis*. The deliberate distribution of anthrax spores through US mail system in 2001 resulted in 5 deaths among the 11 individuals who contracted inhalational anthrax, which highlight the great threat posed by the potential use of anthrax in terrorism and warfare. The lethality of inhalational anthrax is primarily due to the action of anthrax toxins. Bacterium produces three toxin components; they are protective antigen (PA), lethal factor (LF), and edema factor (EF). PA together with LF forms lethal toxin (LT) and PA together with EF forms edema toxin (ET). PA functions as a vehicle to mediate the cellular uptake of the LF and EF. LF is a metalloenzyme that cleaves mitogen-activated protein kinase kinases (MEKs) and can replicate symptoms of anthrax disease when injected in animals with PA. EF is a calcium-calmodulin-dependent adenylate cyclase with a range of toxic effects in the host. These toxins are the dominant virulence factors for anthrax disease.

Currently there are no approved therapies for anthrax disease except antibiotics. Treatment with antibiotics, though, has considerable limitations. Exposure to the bacterium followed by bacterial division leads to the production of large quantities of the anthrax toxins. Thus, unless exposure is diagnosed early enough for vigorous antibiotic treatment, patients will succumb to disease even after the killing of all bacteria. The current vaccine approved by US Food and Drug Administration is also not effective in protecting newly infected individuals, as it requires repeated administration and at least 4 weeks for development of protective titers.

International Patent Application WO2004/087042 and U.S. Pat. No. 8,324,355 teaches the generation of antibodies targeted at the catalytic zinc ion and the enzyme surface of MMPs which are naturally expressed in animals.

U.S. Patent Application No. 20100119520 teaches monoclonal antibodies directed against anthrax lethal factor.

U.S. Patent Application No. 20100227335 teaches monoclonal antibodies directed against MMP-7.

SUMMARY OF THE INVENTION

According to an aspect of some embodiments of the present invention there is provided an antibody comprising an antigen recognition region which binds a catalytic site of anthrax lethal factor (ALF), wherein the antibody inhibits the activity of the ALF.

According to an aspect of some embodiments of the present invention there is provided an antibody comprising an antigen recognition region which binds a catalytic site of MMP-7, wherein the antibody inhibits the activity of the MMP-7 and wherein the Ki of the antibody towards the MMP-7 is at least 5 times lower than a Ki of the antibody towards MMP2 or MMP9.

According to an aspect of some embodiments of the present invention there is provided a method of generating an antibody which inhibits a metalloenzyme, the method comprising immunizing a subject with:

(i) a synthetic zinc mimicry compound having structural and electronic properties similar to a catalytic domain of the metalloenzyme; and (ii) the metalloenzyme, thereby generating the antibody which inhibits the metalloenzyme.

According to an aspect of some embodiments of the present invention there is provided a hybridoma cell line expressing an antibody which recognizes anthrax.

According to an aspect of some embodiments of the present invention there is provided a hybridoma cell line expressing an antibody which recognizes MMP-7.

According to an aspect of some embodiments of the present invention there is provided a monoclonal antibody produced by the anthrax hybridoma cell line.

According to an aspect of some embodiments of the present invention there is provided a monoclonal antibody produced by the MMP-7 hybridoma cell line.

According to an aspect of some embodiments of the present invention there is provided a method of treating a disease associated with imbalanced or abnormal activity of MMP-7 in a subject in need thereof, the method comprising administering to the subject a therapeutically effective amount of the antibody against MMP-7, thereby treating the disease associate with imbalanced or abnormal activity of MMP-7 in the subject.

According to an aspect of some embodiments of the present invention there is provided an method of diagnosing a disease associated with imbalanced or abnormal activity of MMP-7 in a subject, the method comprising contacting a sample of the subject with the antibody of the present invention so as to analyze expression of MMP-7, wherein an upregulation of expression of the MMP-7 is indicative of the disease associated with imbalanced or abnormal activity of MMP-7.

According to an aspect of some embodiments of the present invention there is provided a method of treating or preventing anthrax disease in a subject in need thereof, the method comprising administering to the subject a therapeutically effective amount of the antibody of the present invention, thereby treating or preventing the anthrax disease.

According to an aspect of some embodiments of the present invention there is provided a method of diagnosing anthrax infection in a subject, the method comprising contacting a sample of the subject with the antibody of the present invention so as to analyze expression of ALF, wherein an expression of the ALF is indicative of anthrax infection.

According to an aspect of some embodiments of the present invention there is provided a pharmaceutical composition comprising the antibody of the present invention.

According to some embodiments of the invention, the antigen recognition region binds a compound having the general Formula (I):

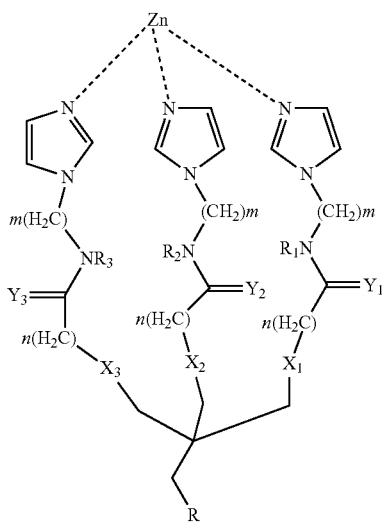

wherein:
m and n are each independently an integer from 1 to 6;
$X_1$-$X_3$ and $Y_1$-$Y_3$ are each independently O or S;
$R_1$-$R_3$ are each independently selected from the group consisting of hydrogen, alkyl, and cycloalkyl; and
R is $(CH_2)_x$-$C(=O)NR'$—$(CH_2)_y$-NR'R''
whereas:
x and y are each independently an integer from 1 to 6; and
R' and R'' are each independently selected from the group consisting of hydrogen, alkyl, and cycloalkyl.

According to some embodiments of the invention, the antigen recognition region binds the metal ion coordinating amino acids within the catalytic zinc site of the ALF.

According to some embodiments of the invention, the antigen recognition region also binds to the metal ion of the metal ion coordinating amino acids within the catalytic zinc site of the ALF.

According to some embodiments of the invention, the metalloenzyme is MMP-7 or ALF.

According to some embodiments of the invention, the zinc mimicry compound has the general formula (I):

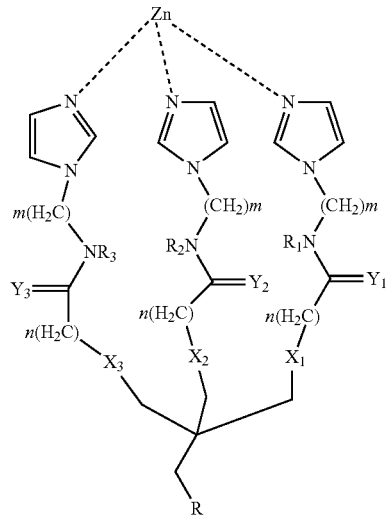

wherein:
m and n are each independently an integer from 1 to 6;
$X_1$-$X_3$ and $Y_1$-$Y_3$ are each independently O or S;
$R_1$-$R_3$ are each independently selected from the group consisting of hydrogen, alkyl, and cycloalkyl; and
R is $(CH_2)_x$-$C(=O)NR'$—$(CH_2)_y$-NR'R''
whereas:
x and y are each independently an integer from 1 to 6; and
R' and R'' are each independently selected from the group consisting of hydrogen, alkyl, and cycloalkyl.

According to some embodiments of the invention, the immunizing is effected by initially immunizing with (i) and subsequently immunizing with (ii).

According to some embodiments of the invention, the immunizing is effected by co-immunizing with (i) and (ii).

According to some embodiments of the invention, the metalloenzyme is not naturally expressed by the subject.

According to some embodiments of the invention, the antibody is attached to a detectable moiety or a therapeutic moiety.

According to some embodiments of the invention, the disease is cancer or an inflammatory bowel disease.

According to some embodiments of the invention, the administering is effected prophylactically.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The patent or application file contains at least one drawing executed in color. Copies of this patent or patent application publication with color drawing(s) will be provided by the Office upon request and payment of the necessary fee.

The present invention, in some embodiments thereof, relates to methods of generating antibodies to metalloenzymes, more particularly, but not exclusively, to MMP-7 and anthrax lethal factor (ALF).

Matrix metalloproteases participate in many biological processes, ranging from cell proliferation, differentiation and remodeling of the extracellular matrix (ECM) to vascularization and cell migration. These processes require a delicate balance between the functions of the matrix metalloproteases (MMPs) and natural tissue inhibitors thereof (TIMPs). The loss of this balance is the hallmark of numerous pathological conditions including metastatic tumors, neurodegenerative diseases and osteoarthritis.

Numerous MMP inhibitors are known in the art including small peptide inhibitors such as hydroxomate, non-microbial tetracyclins and monoclonal antibodies.

The present inventors have previously uncovered that antibodies which recognize both electronic and structural determinants of the catalytic site of metalloenzymes can be used as potent inhibitors thereof. Using haptens which mimic the metal-bound catalytic site of metalloenzymes as immunogens enabled the generation of highly efficient therapeutic antibodies which were shown to be able to treat clinical conditions characterized by elevated metalloprotein activity (see WO2004/087042 and WO2008/102359).

The present inventors have now shown that immunizing with both the mimicking haptens described herein above and the metalloenzyme itself allows for generation of highly selective antibodies (metallobodies).

The present inventors demonstrated the feasibility of this immunization approach by immunizing with a) Imisdp as the mimicking hapten and MMP-7 as the metalloenzyme; and b) Imisdp as the mimicking hapten and anthrax lethal factor as the metalloenzyme. Antibodies directed towards either MMP-7 or anthrax lethal factor (ALF) were produced—see FIGS. 1A-D.

These results demonstrate the generality of the present immunization approach and the feasibility of producing metallobodies targeted at a selected metalloenzyme.

Thus according to one aspect of the present invention there is provided a method of generating an antibody (or a fragment thereof) which inhibits a metalloenzyme, the method comprising immunizing a subject with:

(i) a synthetic zinc mimicry compound having structural and electronic properties similar to a catalytic domain of the metalloenzyme; and (ii) the metalloenzyme, thereby generating the antibody which inhibits the metalloenzyme.

Examples of metalloenzymes which may be inhibited using the teachings of the present invention, include but are not limited to, neutrophil collagenase, collagenase-3, gelatinase A, gelatinase B, stromelysins-2 and 3, matrilysin, macrophage elastase; membrane-type MMPs, aggrecanase, cytokine convertases, adhesion molecule "shedding enzymes", endothelin converting enzyme, angiotensin converting enzyme, neutral endopeptidase, FTSH—bacterial metalloprotease, metallo-lactamase (carbapenases), bacterial toxins e.g., anthrax lethal factor, tetanus or botulism toxins, ras farnesyl protein transferase, carbonic anhydrase and the like. Other examples of metalloenzymes are disclosed in Hodgson, Bio/Technology, 13:554 (1995); Gordon, et al., Clin. Exper. Rheum., 11(8):S91-S94 (1993); Ray, et al., Eur. Respir. J., 7:2062-2072 (1994); O'Connor, et al., Thorax, 49: 602-609 (1994); Docherty, et al., Tibtech, Vol. 10, (1992); Newby, et al., Basic Res. Cardiol., 89(Suppl): 59-70; Freije, et al., J. Biol. Chem., 269(24):16766-16773 (1994); Shapiro, et al., J. Biol. Chem., 268(32):23824-23829 (1993); Belaauoaj, et al., J. Biol. Chem., 27(24):14568-14575 (1995); Gearing, et al., Letters to Nature, Nature, 370:555-557 (1994); McGeehan, et al., Letters to Nature, Nature, 370:558-561 (1994); Mohler, et al., Letters to Nature, Nature, 370:218-220 (1994); Sato, et al., Letters to Nature, Nature, 370:61-65 (1994); Crowe, et al., J. Exp. Med., 181:1205-1210 (1995); Payne, J. Med. Microbiol., 32:93-99 (1993); Deshpande, et al., Toxicon, 33(4):551-557 (1995); DePhillips, et al., Eur. J. Biochem., 229:61-69 (1995).

Figure 1A:
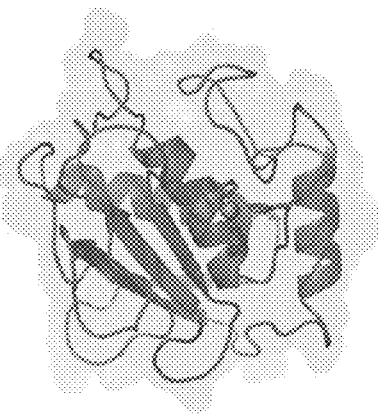
FIGS. 1A-D illustrate isolation of cross reactive mAbs recognizing both synthetic mimicry molecule and a targeted zinc dependent metalloenzyme. A. Cross-reactivity of the mAbs raised by immunization against synthetic Zn-mimicry antigen followed by human MMP-7. The affinity of antibodies from hybridoma supernatant in different dilutions was determined by a direct antigen ELISA, on which were absorbed synthetic Zn-mimicry epitope, human MMP-7 or BSA as antigens. B. Cross-reactivity of the mAbs raised by immunization against synthetic Zn-mimicry antigen followed by Anthrax Lethal Factor. The affinity of antibodies from hybridoma supernatant in different dilutions was determined by a direct antigen ELISA, on which were absorbed synthetic mimicry Zn-epitope, Anthrax Lethal Factor or BSA as antigens. C. human MMP-7 catalytic domain shown in secondary structure representation with semi-transparent surface, zinc ion (orange sphere), catalytic site histidines are shown as sticks (PDB:1MMQ). D. Anthrax Lethal Factor catalytic domain shown in secondary structure representation with semi-transparent surface, zinc ion (orange sphere), catalytic site histidines and glutamic acid are shown as sticks (PDB: 1J7N).

According to one embodiment the metalloenzyme is not naturally expressed by the subject (or expressed at low levels). Such metalloenzymes include MMP-7, and bacterial toxins (e.g. anthrax lethal factor).

Synthetic zinc mimicry compounds having structural and electronic properties similar to a catalytic domain of the metalloenzyme are typically compounds which comprise chelated metal ions. The metal ion is typically Zinc or its analogous ions Cobalt or Cademium.

According to one embodiment, the chelator is porphyrin.

The zinc mimicry compound may be selected based upon the structural and electronic properties of the actual catalytic domain in the target polypeptide. Typically, the target polypeptide includes 3 amino acids which provide three contact points required for the transition metal coordination. Representative coordination complex geometries can be tetrahedral, square planar or trigonal depending upon the transition metal ion. In general the mimicking compositions of the present invention are selected based upon the amino acid side chain structure and the geometry of coordination. Typically, amino acids which can coordinate transition metal binding are histidine, arginine, glutamate, cysteine, methionine, tryptophan, serine, threonine and tyrosine, with the first two being preferable.

Exemplary synthetic zinc mimicry compounds are disclosed in WO2004/087042 and WO2008/102359, incorporated herein by reference.

According to one embodiment the synthetic zinc mimicry compound has the general Formula (I):

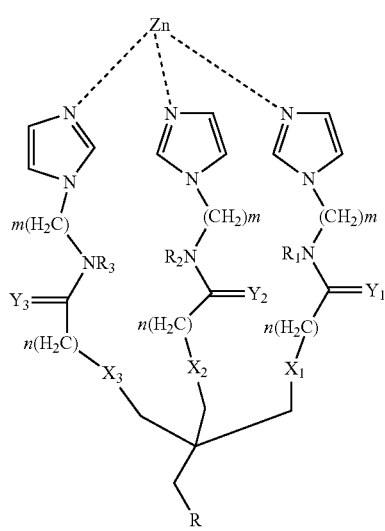

wherein:
m and n are each independently an integer from 1 to 6;
$X_1$-$X_3$ and $Y_1$-$Y_3$ are each independently O or S;
$R_1$-$R_3$ are each independently selected from the group consisting of hydrogen, alkyl, and cycloalkyl; and
R is $(CH_2)x$-$C(=O)NR'$—$(CH_2)y$-NR'R"
whereas:
x and y are each independently an integer from 1 to 6; and
R' and R" are each independently selected from the group consisting of hydrogen, alkyl, and cycloalkyl.

According to a preferred embodiment of this aspect of the present invention the compound is [2-(2-minoethylcarbomoyl)-ethoxymethyl]-tris-[2-(N-(3-imidazol-1-yl-propyl))-ethoxymethyl]methane, termed, Imisdp, having the general Formula (II):

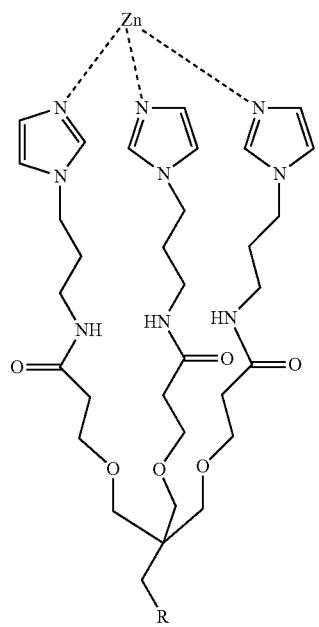

wherein R=—$CH_2$—$C(=O)NH$—$CH_2$—$CH_2$—$NH_2$

As mentioned, the method of the present invention is carried out by immunizing with both the zinc mimicry compound described herein above and the metalloenzyme itself.

The present invention contemplates immunization with the full-length metalloenzyme or portions thereof. Typically, the portion should contain an antigenic determinant (i.e. epitope) which is specific to that particular metalloenzyme.

According to one embodiment, the antigenic determinant is on the surface of the metalloenzyme.

The metalloenzyme used for immunization may be purified from its in vivo environment or alternatively may be generated through recombinant means.

According to one embodiment, the immunization procedure comprises initial immunization with the zinc mimicry compound and subsequent (e.g. three-twelve weeks later) immunization with the metalloenzyme. The exact time of immunization may be determined by checking to see if an immune response is present in the immunized animal (e.g. mouse). For instance the titre of antibodies in the serum may be analyzed.

According to another embodiment, the immunization procedure comprises initial immunization with the metalloenzyme and subsequent (e.g. three-twelve weeks later) immunization with the zinc mimicry compound.

According to yet another embodiment, the immunization procedure comprises co-immunization with both the metalloenzyme and the zinc mimicry compound.

As used herein the term "antibody", refers to an intact antibody molecule and the phrase "antibody fragment" refers to a functional fragment thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

In cases where the invention compounds are too small to elicit a strong immunogenic response, such antigens (haptens) can be coupled to antigenically neutral carriers such as keyhole limpet hemocyanin (KLH) or serum albumin [e.g., bovine serum albumine (BSA)] carriers (see U.S. Pat. Nos. 5,189,178 and 5,239,078 and Examples 2 of the Examples section). Coupling to carrier can be effected using methods well known in the art; For example, direct coupling to amino groups can be effected and optionally followed by reduction of imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Once antibodies are obtained, they may be tested for metalloenzyme inhibitory activity and affinity. Appropriate assay conditions for metalloprotein inhibition activity are described in Knight et al., FEBS Letters 296(3):263-266 (1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm., 139: 1184-1187 (1984) and U.S. Pat. Nos. 4,743,587 and 5,240,958.

As mentioned, using the above-methodology, the present inventors were able to produce an antibody that recognized anthrax lethal factor (ALF) and an additional antibody that recognized MMP-7.

Thus according to another aspect of the present invention there is provided an antibody comprising an antigen recognition region which binds a catalytic site of anthrax lethal factor (ALF), wherein the antibody inhibits the activity of the ALF.

According to still another aspect of the present invention there is provided an antibody comprising an antigen recognition region which binds a catalytic site of MMP-7, wherein the antibody inhibits the activity of the MMP-7.

The antibodies of this aspect of the present invention typically have a very high binding affinity and specificity towards MMP-7 with an $EC_{50}$ of about 1-500 nM, more typically of about 1-250 nM, more typically of about 1-100 nM and even more typically of about 1-50 nM. The antibodies of this aspect of the present invention typically exhibit a tight binding inhibition pattern towards MMP-7 (Ki=1-500 nM and more preferably 50-200 nM), the Ki being at least 2 times, at least 5 times or even at least 10 times lower than the Ki of the antibody towards other MMPs such as MMP2, MMP9 or MMP14.

The antibody may bind to the metal-coordinating ions of the catalytic site and not to the metal ion itself or alternatively the antibody may bind to both the metal ion and its coordinating ions present in the active site pocket.

According to another aspect of the present invention there is provided a monoclonal antibody produced from the hybridoma cell lines exemplified in Example 1 herein below.

The present invention also provides for any (poly)peptide sequence which comprises at least one of the CDR sequences of these antibodies as well as homologs and fragments thereof as long as its metalloenzyme inhibitory activity is retained (specific inhibition of the catalytic activity of the metalloprotein). An example of such a polypeptide is an antibody (see above).

The term "polypeptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, Tic, naphtylalanine (Nal), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |

TABLE 2-continued

| Non-conventional amino acid | Code | Non-conventional amino acid | Code |
|---|---|---|---|
| D-α-methylarginine | Dnmarg | N-cyclopropylglycine | Ncpro |
| D-α-methylasparagine | Dnmasn | N-cycloundecylglycine | Ncund |
| D-α-methylaspartate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenyl ethylamino)cyclopropane | Nmbc | | |

Peptides with improved affinity to a metalloenzyme of interest or enhanced biological activity may be generated by methods well known in the art including phage display and computational biology.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, to Academic Press (New York). For a review of classical solution synthesis, see Schroder, G. and Lupke, K. (1965). The Peptides, vol. 1, Academic Press (New York). For recombinant techniques see references further below.

According to some embodiments of the invention, the antibody may be conjugated to a functional moiety (also referred to as an "immunoconjugate") such as a detectable or a therapeutic moiety. The immunoconjugate molecule can be an isolated molecule such as a soluble and/or a synthetic molecule.

Various types of detectable or reporter moieties may be conjugated to the antibody of the invention. These include, but not are limited to, a radioactive isotope (such as $^{[125]}$ iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., to "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol. Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum to Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 3 provides non-limiting examples of identifiable moieties which can be conjugated to the antibody of the invention.

TABLE 3

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR | |
| orange fluorescent protein | AAL33917 | AF435432 |
| Beta galactosidase | ACH42114 | EU626139 |
| Streptavidin | AAM49066 | AF283893 |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 4, hereinbelow.

TABLE 4

| Therapeutic moiety | Amino acid sequence (GenBank Accession No) | Nucleic acid sequence (GenBank Accession No) |
| --- | --- | --- |
| *Pseudomonas* exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

The functional moiety (the detectable or therapeutic moiety of the invention) may be attached or conjugated to the antibody of the invention in various ways, depending on the context, application and purpose.

When the functional moiety is a polypeptide, the immunoconjugate may be produced by recombinant means. For example, the nucleic acid sequence encoding a toxin (e.g., PE38 KDEL) or a fluorescent protein [e.g., green fluorescent protein (GFP), red fluorescent protein (RFP) or yellow fluorescent protein (YFP)] may be ligated in-frame with the nucleic acid sequence encoding the antibody of the invention and be expressed in a host cell to produce a recombinant conjugated antibody. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Exemplary methods for conjugating peptide moieties (therapeutic or detectable moieties) to the antibody of the invention are described herein below:

SPDP Conjugation—

A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation—

A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide Conjugation—

Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

As is mentioned hereinabove, one specific use for an antibody directed against MMP-7 is prevention or treatment of diseases associated with imbalanced or abnormal activity of MMP-7.

Examples of such disease include, but are not limited to, arthritic diseases, such as osteoarthritis (OA), rheumatoid arthritis (RA), septic arthritis, soft tissue rheumatism, polychondritis and tendonitis; metastatic tumors, periodontal diseases; corneal ulceration, such as induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; pulmonary emphysema, wound healing and HIV infection.

According to one embodiment the disease is cancer. Exemplary cancers include ovarian cancer, renal cell carcinoma, colon cancer, breast cancer, gastric cancer, rectal cancer and prostate cancer.

According to another embodiment the disease is inflammatory bowel diseases (IBD) which are severe gastrointestinal disorders characterized by intestinal inflammation and tissue remodeling, that increase in frequency and may prove disabling for patients. The major forms of IBD, ulcerative colitis (UC) and Crohn's disease are to chronic, relapsing conditions that are clinically characterized by abdominal pain, diarrhea, rectal bleeding, and fever.

Subjects which may be treated include mammalian subjects such as humans.

Another use for an antibody directed against MMP-7 is diagnosis of a disease associated with an upregulation of expression of MMP-7.

Thus, according to another aspect of the present invention there is provided a method of diagnosing a disease associated with imbalanced or abnormal activity of MMP-7 in a subject, the method comprising contacting a sample of the subject with an antibody described herein so as to analyze expression of MMP-7, wherein an upregulation of expression of the MMP-7 is indicative of the disease associated with imbalanced or abnormal activity of MMP-7.

Methods of analyzing expression of MMP-7 using the disclosed antibody include, but are not limited to Western analysis, immunoprecipitation and immunohistochemistry.

A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

Typically the amount of MMP-7 is compared with a control (a corresponding sample from a healthy subject) or known amounts of MMP-7 which correspond to a healthy subject).

Following the diagnosis, the subject may be informed of the outcome. Further additional diagnostic tests may be carried out on the basis of the outcome of the tests using the MMP-7 antibody disclosed herein.

It will be appreciated that as well as performing the diagnosis in vitro (i.e. on samples of the subject), the diagnosis may also be effected in vivo.

Diseases which may be diagnosed include those listed above for diseases which can be treated.

It will be appreciated that a specific use of an antibody directed against anthrax lethal factor is treatment or prevention of anthrax infection.

As used herein, the term "anthrax" refers to a disease caused, directly or indirectly, by infection with *Bacillus anthracis*. Inhalation: Initial symptoms may resemble a common cold—sore throat, mild fever, muscle aches and malaise. After several days, the symptoms may progress to severe breathing problems and shock. Inhalation anthrax is usually fatal. Cutaneous: Anthrax infections can occur when the bacterium enters a cut or abrasion on the skin, such as when handling contaminated wool, hides, leather or hair products (especially goat hair) of infected animals. Skin infection begins as a raised itchy bump that resembles an insect bite but within 1-2 days develops into a vesicle and then a painless ulcer, usually 1-3 cm in diameter, with a characteristic black necrotic (dying) area in the center. Lymph glands in the adjacent area may swell. About 20% of untreated cases of cutaneous anthrax will result in death. Gastrointestinal: The intestinal disease form of anthrax may follow the consumption of contaminated meat and is characterized by an acute inflammation of the intestinal tract. Initial signs of nausea, loss of appetite, vomiting, fever are followed by abdominal pain, vomiting of blood, and severe diarrhea. Intestinal anthrax results in death in 25% to 60% of cases.

The treatment may be effected following anthrax infection or may be used as a prophylactic prior to an anticipated infection.

In some embodiments, monoclonal antibodies disclosed herein may be used individually or in combination with other antibodies in detection, prophylaxis and/or as therapy for anthrax disease in humans. For example, a cocktail of neutralizing antibodies against all three components (PA, LF, and EF) of anthrax toxin can be used in detection, prophylaxis and/or as therapy. Alternatively, pair-wise combinations can be used. For example, a therapy may include anti-PA antibodies and anti-LF antibodies; anti-PA and anti-EF antibodies; or anti-LF and anti-EF antibodies. Anti-PA antibodies that may be used in embodiments disclosed herein include, but is not limited to, those described in PCT Publication No. WO2007/084107, which is herein incorporated by reference in its entirety.

It will be appreciated that antibodies which recognize anthrax lethal factor (ALF) may also be used to diagnose an anthrax infection.

Methods of analyzing expression of ALF using the disclosed antibody include, but are not limited to Western analysis, immunoprecipitation and immunohistochemistry.

A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

Detection of any amount of ALF above background level may indicate an anthrax infection.

It will be appreciated that as well as performing the diagnosis in vitro (i.e. on samples of the subject), the diagnosis may also be effected in vivo. Following the diagnosis, the subject may be informed of the outcome. Further additional diagnostic tests may be carried out on the basis of the outcome of the tests using the MMP-7 antibody disclosed herein.

The antibodies of the present invention may be administered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct to intraventricular, intracardiac, e.g., into the right or left ventricular cavity, into the common coronary artery, intravenous, inrtaperitoneal, intranasal, or intraocular injections.

Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly to concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (antibody) effective to prevent, alleviate or ameliorate symptoms of a disorder (e.g., cancer/anthrax infection) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue or blood levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

The terms "comprises", "comprising", "includes", "including", "having" and their conjugates mean "including but not limited to".

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, to Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Antibodies which Recognize MMP-7 or Anthrax Lethal Factor

Materials and Methods

Synthesis of Zn-Tripod:

A.

Pentaerythritol (9.53 g, 0.07 mol) and NaOH (0.7 mL of 30% w/w) were mixed in a flask and acrylonitrile (20.3 mL, 0.44 mol) was slowly added so that the temperature did not exceed 30° C. The mixture was stirred over-night at room temperature, neutralized with 1 N HCl, extracted into EtOAc (200 mL), washed twice with water, dried over Na$_2$SO$_4$, and concentrated. 22.9 g of the tetranitrile derivative was obtained (94% yield).

B.

The tetranitrile 1 (7.22 g, 0.021 mol) was treated with concentrated HCl (10 mL), refluxed for 4 h at 95° C., extracted into cold EtOAc (300 mL), washed twice with water, dried over Na$_2$SO$_4$, and concentrated. The tetra acid (6.67 g) was obtained in 75% yield.

C and D

SOCl$_2$ (11.9 mL) was added to the tetra acid 2 (11.5 g) and the solution was warmed to 40° C. for 15 hours (overnight). Excess thionyl chloride was distilled and the residue, the crude tetraacyl halide, was dissolved in dry CHCl$_3$ (30 ml). Pentachlorophenol (28.76 g) was added, the mixture was cooled to 0° C., Et$_3$N (15 mL, 0.108 mol) was added and the mixture was stirred at room temperature. The reaction was followed by IR to see that the peak of the chloride disappeared (about 1 day). The solvent was removed and the residue was purified by flash chromatography (silica gel, eluent CHCl$_3$). Residual pentachloro phenol was removed by filtration over deactivated neutral alumina to yield 11.94 g (8.42 mmoles, 31% yield) of the tetra active ester IR (CDCl$_3$): ν=1783 cm$^{-1}$ (COOC$_6$—Cl$_5$).

$^1$H NMR (CDCl$_3$) δ=3.81 (t, J) 6 Hz, 8H, CCH$_2$OCH$_2$), 3.46 (s, 8H, CCH2O), 2.91 (t, J) 6 Hz, 8H, CH$_2$CN).

solved in 20 ml of dry dichloromethane. The solution was stirred overnight while the pH was kept at ~8 with triethyl amine. The solvent was removed and the residue purified by flash chromatography with chloroform: ethyl acetate (90:10) to give (152 mg, 15% yield) of compound 4.

$^1$H NMR 250 MHz (CDCl$_3$): δ=1.4 (s, 9H, Boc); 2.4 (t, 2H, J=6 Hz, —CH$_2$—CH$_2$—CONH); 2.9 (t, 6H, J=6 Hz, —CH$_2$—CH$_2$—COOPCP); 3.2 (q, 2H, J=6 Hz, —CONH—CH—CH$_2$—CH$_2$—NHBoc); 3.31 (t, 2H, J=6 Hz, —CONH—CH$_2$—CH$_2$—NHBoc); 3.38 (s, 2H, —C—CH$_2$—O—CH$_2$—CH$_2$—CONH—); 3.42 (s, 6H, —C—CH$_2$—O—CH$_2$—CH$_2$—COOPCP); 3.61 (t, 2H, J=6 Hz, —C—CH$_2$—O—CH$_2$—CH$_2$—CONH—); 3.78 (t, 6H, J=6 Hz, —C—CH$_2$—O—CH$_2$—CH$_2$—CONH); 5.03 (t, 1H, NH); 6.7 (t, 1H, NH).

F.

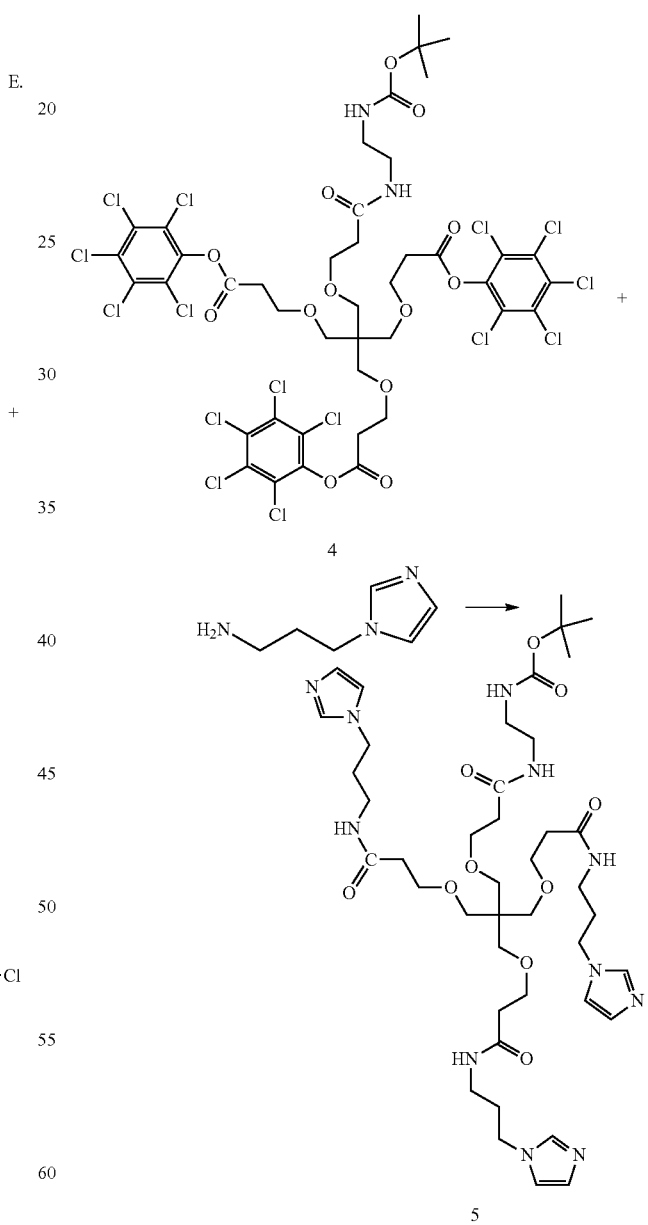

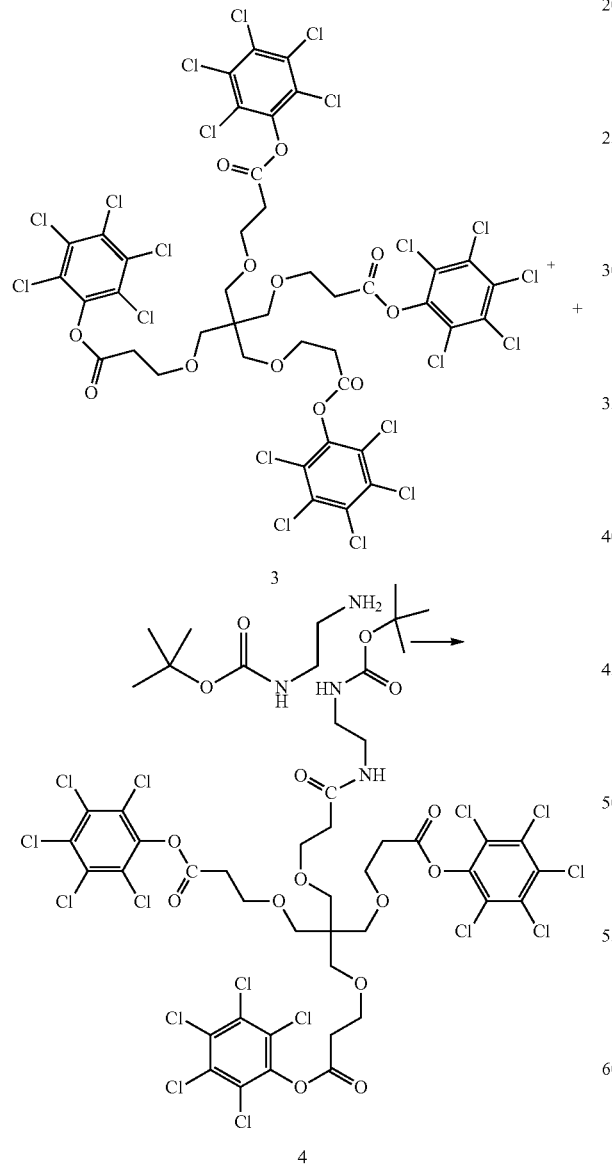

The tetra active ester 3 (1 g, 0.69 mmole) and mono-BOC-ethylenediamine (100 mg, 0.62 mmole) were dis- Compound 4 (150 mg, 0.11 mmole) and 1-(3-aminopropyl)-imidazole (33 μl, to 0.39 mmole) ertr dissolved in dry THF (20 ml) and stirred overnight at room temperature. The solvent was removed and the residue was purified by column chromatography with chloroform:methanol (5:9) as eluents.

The product 5, 45 mg, was obtained in 44% yield.

$^1$H NMR 250 MHz (CDCl$_3$/MeOD) δ=1.45 (s, 9H, Boc); 2.0 (m, 6H, J=6 Hz, —CONH—CH$_2$—CH$_2$—CH$_2$-imi); 2.4 (t, 6H, J=6 Hz, —O—CH$_2$—CH$_2$—CONH—); 2.5 (t, 2H, J=6 Hz, —CH$_2$—CH$_2$—CONH—CH$_2$—CH$_2$—NHBoc) 3.0 (m, 8H, J=6 Hz, —CONH—CH$_2$—CH$_2$—CH$_2$-imi, —CH$_2$—CH$_2$—CONH—CH$_2$—CH$_2$—NHBoc); 3.1 (t, 2H, J=6 Hz, —CONH—CH$_2$—CH$_2$—NHBoc); 3.4 (b, 8H, —C—CH$_2$—O—CH$_2$—CH$_2$—CONH—CH$_2$—CH$_2$—NH-Boc, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NH-Boc,); 4.0 (t, 6H, J=6 Hz, —CONH—CH$_2$—CH$_2$—CH$_2$-imi); 5.5 (t, 1H, NH); 6.98 (s, 3H, Imi); 7.06 (s, 3H, Imi) 7.32 (t, 3H, NH); 7.57 (s, 3H, Imi). ESI-MS: 910.87 [M+Na]$^+$, 925.98 [M+K]+.

G.

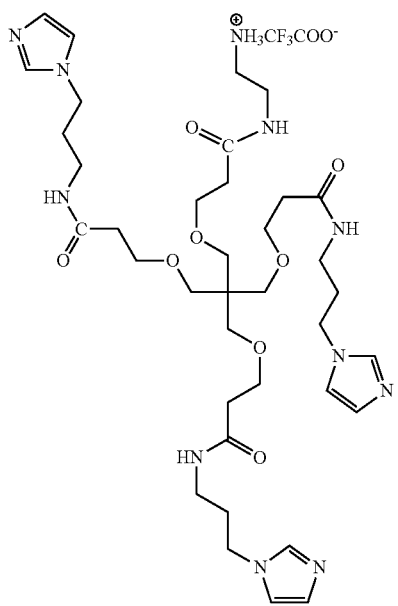

6

The tris(imidazole) derivative 5 (40 mg, 0.045 mmole) was dissolved in a 2:1 solution of dichloromethane and trifluoroacetic acid (6 ml) and stirred for an hour. The solvent was removed and excess of TFA was further removed by co-evaporation with carbon tetrachloride. The product, 6, 30 mg, was obtained in 85% yield.

$^1$H NMR 250 MHz (CDCl$_3$/MeOD) δ=1.9 (m, 6H, J=6 Hz, —CONH—CH$_2$—CH$_2$—CH$_2$-imi); 2.3 (m, 8H, J=6 Hz, —O—CH$_2$—CH$_2$—CONH—, —CH$_2$—CH$_2$—CONH—CH$_2$—CH$_2$—NH$_2$); 2.9 (t, 2H, J=6 Hz, —CONH—CH$_2$—CH$_2$—CH$_2$-imi); 3.0 (t, 2H, J=14 Hz, —CONH—CH$_2$—CH$_2$—NH$_2$); 3.31 (t, 2H, J=6 Hz, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NH$_2$); 4.0 (t, 6H, J=6 Hz, —CONH—CH$_2$—CH$_2$—CH$_2$-imi); 7.26 (s, 3H, Imi); 7.32 (s, 3H, Imi); 8.82 (s, 3H, Imi)

H. Zn(II) Complex of the Tripod 6.

The tripod 6 (30 mg) was dissolved in methanol (1 ml). 1N NaOH (1-2 drops) was added followed by a solution of ZnCl$_2$ (5 mg) in methanol and the solution is stirred for half an hour. A white precipitate was obtained and filtered. The complex (12 mg) was obtained in 37% yield.

$^1$H NMR 250 MHz (MeOD/D$_2$O) δ=1.8 (m, 6H, J=6 Hz, —CONH—CH$_2$—CH$_2$—CH$_2$-imi); 2.4 (m, 8H, J=6 Hz, —O—CH$_2$—CH$_2$—CONH—, —CH$_2$—CH$_2$—CONH—CH$_2$—CH$_2$—NH$_2$); 3.0 (t, 2H, J=6 Hz, —CONH—CH$_2$—CH$_2$—CH$_2$-imi); 3.0 (t, 2H, J=6 Hz, —CONH—CH$_2$—CH$_2$—NH$_2$); 3.31 (b, 2H, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, —C—CH$_2$—O—CH$_2$—CH$_2$—CONH—, —C—CH$_2$—O—CH$_2$—CH$_2$—CONH—CH$_2$—CH$_2$—NH$_2$); 4.2 (b, 6H, —CONH—CH$_2$—CH$_2$—CH$_2$-imi); 7.19 (s, 3H, Imi); 7.28 (s, 3H, Imi); 8.55 (s, 3H, Imi) ESI-MS: 852.09[M+1]$^+$.

Preparation of Zn-Tripod-Protein Conjugates:

Zn-Tripod was conjugated to keyhole limpet hemocyanin (KLH) for immunization and to bovine serum albumin (BSA) for capture of specific antibodies. Zn-Tripod (4 mg) was dissolved in saturated solution of NaHCO$_3$ (0.5 ml), 1-ethyl-3-(3'-dimethylaminopropyl) carbodiimide (4 mg) was added to the solution under stirring. Similarly KLH (at 50:1 molar ratio) or BSA (at 25:1 or 10:1 molar ratio), both in PBS buffer were added to the solution under stirring. After 3 h in RT and overnight in 4° C., conjugates were dialyzed extensively (2×PBS) and diluted to a final concentration of 1 mg/ml. The hapten density (number of hapten molecules per BSA or KLH molecule) of Zn-Tripod was determined by measurement of the zinc content by inductively coupled plasma atomic emission spectroscopy using the ICP-AES model "Spectroflame" from Spectro (Kleve, Germany). The samples were digested with 5% nitric acid in metal-free water, and the volume was adjusted to 6 ml. The zinc content of the sample was determined relative to its equivalent protein concentration.

Preparation of Anti-MMP Metallobodies Using Zn-Tripod-KLH as an Immunogen:

Female BALB/c mice were immunized on day 1 with complete Freund adjuvant and 30 µg of Zinc-Tripod-KLH followed (after 3 to 4 boosts with Zinc-Tripod, once an immune response toward Zinc-Tripod can be detected in the mice serum by ELISA) by a second immunization with the whole target metalloenzyme e.g. human MMP-7 or Anthrax Lethal Factor bacterial protease catalytic fragment (Anthrax LF). Hybridomas secreting antibodies cross reactive with the synthetic Zn-mimicry epitope and the metalloenzyme target were isolated.

Boosting was performed every two to three weeks first with incomplete Freund adjuvant by emulsifying and intraperitoneal injection followed by boosts in PBS. Spleen cells from the immunized mice were fused with NSO murine myeloma cells and cultured in HAT (hypoxantine/aminopterin/thymidine) selection medium.

The culture supernatants of the hybridoma were screened using an ELISA, employing pairs of wells in microtiter plates on which were absorbed MMP-7, anthrax lethal factor and Zinc-Tripod-BSA as antigens (0.5 μg of MMP-7, anthrax lethal factor or Zinc-Tripod-BSA conjugate per well). After incubation with 100 μl of the hybridoma supernatants, and with intervening washes with Tris-buffered saline, pH 7.5, containing 0.05% polysorbate 20 (TWEEN™ 20), the wells were incubated with a peroxidase-conjugated goat anti-mouse IgG, followed by a substrate solution containing 2'-azino-bis(3-ethylbenzthiazoline-6-sulfonic acid) diammonium salt.

Results

Figure 1B:
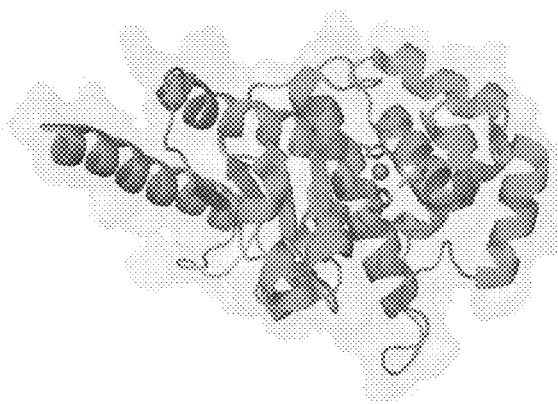
Figure 1C:
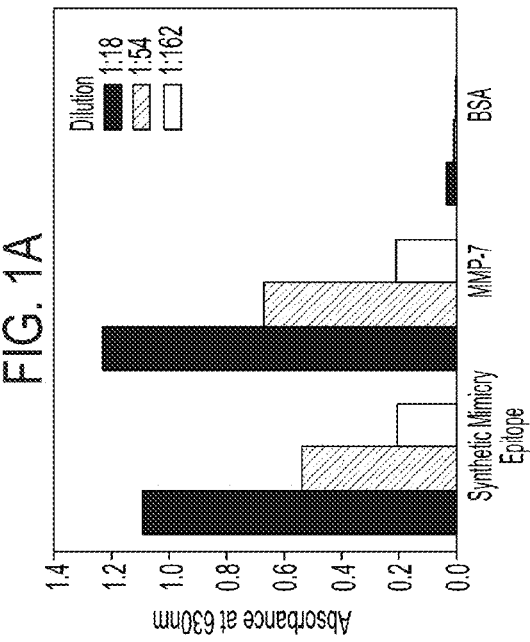
Figure 1D:
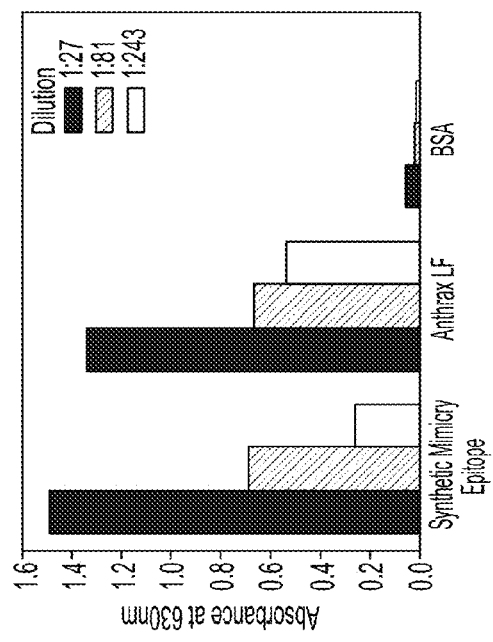

Mice were immunized with both synthetic zinc-protein mimicry compound followed by the whole target metalloenzyme. This immunization procedure yielded cross reactive hybridoma which secrete monoclonal antibodies recognizing both the synthetic mimicry molecule and the target metalloenzyme (FIGS. 1A-D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody comprising an antigen recognition region which binds to the synthetic zinc-mimicry epitope

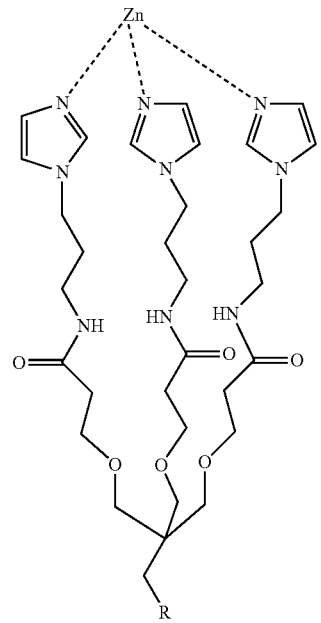

wherein R is O—CH$_2$—CH$_2$—CONH—CH$_2$—CH$_2$—NH$_2$, wherein said antibody is obtainable by immunizing a subject with:
   (i) said synthetic zinc-mimicry epitope; and
   (ii) matrix metalloproteinase-7 (MMP-7).

2. The antibody of claim 1 attached to a detectable moiety or a therapeutic moiety.

3. A pharmaceutical composition comprising the antibody of claim 1.

4. A method of detecting MMP-7 expression in a subject, the method comprising contacting a sample from the subject with the antibody of claim 1, and detecting expression of MMP-7.

* * * * *